United States Patent
Blick

(10) Patent No.: US 7,485,857 B2
(45) Date of Patent: Feb. 3, 2009

(54) MICROCOAXIAL PROBES MADE FROM STRAINED SEMICONDUCTOR BILAYERS

(75) Inventor: Robert H. Blick, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 330 days.

(21) Appl. No.: 11/519,212

(22) Filed: Sep. 11, 2006

(65) Prior Publication Data

US 2008/0061798 A1   Mar. 13, 2008

(51) Int. Cl.
| | |
|---|---|
| G12B 21/02 | (2006.01) |
| G12B 21/04 | (2006.01) |
| G12B 21/08 | (2006.01) |
| G01N 13/10 | (2006.01) |
| G01N 13/12 | (2006.01) |
| G01N 13/16 | (2006.01) |

(52) U.S. Cl. .......................... 250/306; 250/307; 73/105; 324/637; 324/638; 977/875; 977/878; 977/879

(58) Field of Classification Search ................. 250/306, 250/307; 73/105; 324/637, 638; 977/875, 977/878, 879
See application file for complete search history.

(56) References Cited

U.S. PATENT DOCUMENTS

| | | | | |
|---|---|---|---|---|
| 5,504,366 A | * | 4/1996 | Weiss et al. | ................. 250/306 |
| 5,559,328 A | * | 9/1996 | Weiss et al. | ................. 250/306 |
| 5,821,410 A | | 10/1998 | Xiang et al. | |
| 2003/0034453 A1 | | 2/2003 | Ookubo et al. | |

OTHER PUBLICATIONS

Feenstra, B.J., et al., "Near-Field Scanning Microwave Microscopy: Measuring Local Microwave Properties and Electric Field Distributions," Center for Superconductivity Research, Department of Physics, University of Maryland, College Park, MD, Mar. 4, 1998.

Prinz, V. Ya, et al., "Free-standing and overgrown InGaAs/GaAs nanotubes, nanohelices and their arrays," Physica E, vol. 6, 828-831, 2000, published by Elsevier Science B.V.

Golod, S.V., et al., "Fabrication of conducting GeSi/Si micro- and nanotubes and helical microcoils," Semiconductor Science and Technology, vol. 16, 181-185, 2001, published by Institute of Physics Publishing.

Schmidt, O.G., et al., "Free-standing SiGe-based nanopipelines on Si (001) substrates," Applied Physics Letters, vol. 76, No. 21, May 21, 2001.

(Continued)

*Primary Examiner*—Jack I Berman
(74) *Attorney, Agent, or Firm*—Whyte Hirschboeck Dudek SC

(57) ABSTRACT

The present invention provides microcoaxial probes fabricated from semiconductor heterostructures that include strained semiconductor bilayers. The microcoaxial probes are well suited for use as scanning probes in scanning probe microscopy, including scanning tunneling microscopy (STM), atomic force microscopy (AFM), scanning microwave microscopy, or a combination thereof.

23 Claims, 4 Drawing Sheets

OTHER PUBLICATIONS

Prinz, V Ya, et al., "A new technique for fabricating three-dimensional micro- and nanostructures of various shapes," Nanotechnology, vol. 12, 399-402, Nov. 27, 2001, published by Institute of Physics Publishing.

Schmidt, O.G., et al., "Free-standing semiconductor micro- and nano-objects," Materials Science and Engineering C 19, 393-396, 2002.

Schmidt, O.G., "Semiconductor tubes, rods and rings of nanometer and micrometer dimension," Physica E, vol. 13, 969-973, 2002, published by Elsevier Science B.V.

Prinz, A., et al., "Application of semiconductor micro- and nanotubes in biology," Surface Science 532-535, 911-915, 2003, published by Science Direct, Elsevier Science B.V.

Park, Jewook, et al., "Observation of biological samples using a scanning microwave microscope," Ultramicroscopy, vol. 102, 101-106, Sep. 7, 2004, published by Science Direct, Elsevier Science B.V.

Hipps, K.W., "Scanning Tunneling Spectroscopy," A Chapter in *Handbook of Applied Solid State Spectroscopy*, Department of Chemistry and Materials Science Program, Washington State University, Pullman, WA, Mar. 2005.

Huang, M., et al., "Nanomechanical Architecture of Strained Bilayer Thin Films: From Design Principles to Experimental Fabrication," Advanced Materials, vol. 17, Issue 23, pp. 2860-2864, Oct. 19, 2005.

Qin, H., et al., "Formation of microtubes from strained SiGe/Si heterostructures," New Journal of Physics, vol. 7, p. 241, Nov. 29, 2005 (doi: 10.1088/1367-2630/7/1/241).

* cited by examiner

MICROCOAXIAL PROBES MADE FROM STRAINED SEMICONDUCTOR BILAYERS

FIELD OF THE INVENTION

The present invention relates generally to the field of microcoaxial probes for use in scanning microscopy and sensors.

BACKGROUND OF THE INVENTION

The continuing size reduction and speed increases of semiconductor transistor elements creates the need for testing and measurement equipment capable of resolving nano-structures at high sampling speeds. Typically, the desirable spatial resolution of such equipment is on the order of 10 nm or better, while the temporal resolution should exceed 50 GHz. Recent improvements in scanning probe microscopy have made it possible to study the material, electric and magnetic properties of samples on small length scales. However, the probe frequency ranges available for present scanning microscopy probes are limited by the minimum probe diameters that are presently achievable. In addition, the production of conventional coaxial scanning microscopy probes involves separate steps to integrate the coaxial components. Thus, a need exists for a laterally integrated microcoaxial probe that can be easily equipped with signal feeding and reading circuitry.

SUMMARY OF THE INVENTION

The present invention provides microcoaxial probes fabricated from strained semiconductor bilayers. The probes generally include an inner conducting core and an outer conducting shield that is electrically insulated from the conducting core layer. The microcoaxial probes are well-suited for use as scanning probes in scanning probe microcroscopy, including scanning tunneling microscopy (STM), atomic force microscopy (AFM), scanning microwave microscopy, or a combination thereof.

The microcoaxial probes are fabricated from multilayered semiconductor heterostructures that include a bilayer, wherein a lattice mismatch between the semiconductor materials of the first and second semiconductor layers in the bilayer induces a built-in strain. Upon release of the bilayer from a supporting sacrificial layer, this built-in strain causes the bilayer to coil into a tube. The bilayers from which the tubes are made incorporate two (or more) conducting channels, or planes, which provide the conducting core and shield when the bilayer curls into the coiled conducting tube. The conducting channels may be incorporated into the starting multilayered structure, or may be fabricated (e.g., deposited) after tube formation. For example, the conducting channels may be incorporated into the tube from the outset by starting with a multilayered heterostructure that includes one or more doped semiconductor layers and/or embedded low-dimensional electron gas layers in the heterostructure. Alternatively, a conductive material (e.g., a metal strip or film) may be deposited on the inner surface of the tube to form an inner conducting core layer or on the outer surface of the tube to form an outer conducting shield layer.

Strained bilayers of Si and SiGe (i.e., Si/SiGe bilayers) and strained bilayers of InGaAs and GaAs (i.e., InGaAs/GaAs bilayers) are examples of semiconductor bilayers that may be included in the multilayered heterostructures used to form the microcoaxial probes.

The microcoaxial probes are well-suited for use as scanning probes in scanning probe microscopy systems. For example, a microcoaxial probe that tapers into an atomically sharp point at the distal end of the conducting tube may be used as a probe in an STM and/or AFM system. The probe may taper into an atomically sharp tip as a result of the coiling process or may be sharpened after tube formation. For example, a metallic tip may be sharpened by dipping the tip in acetone and immersing the tip in an ultrasonic bath. A microcoaxial probe capable of propagating a microwave signal may be used as a probe in a microwave microscopy system. In some preferred embodiments, microcoaxial probes with a combination of these features are designed for use as probes in a combined STM, AFM and/or microwave spectroscopy system.

Further objects, features and advantages of the invention will be apparent from the following detailed description when taken in conjunction with the accompanying drawings.

BRIEF DESCRIPTION OF THE DRAWINGS

FIGS. 3(b)-(d) show tubes formed from coiled Si/SiGe bilayers.

DETAILED DESCRIPTION

Figure 1:
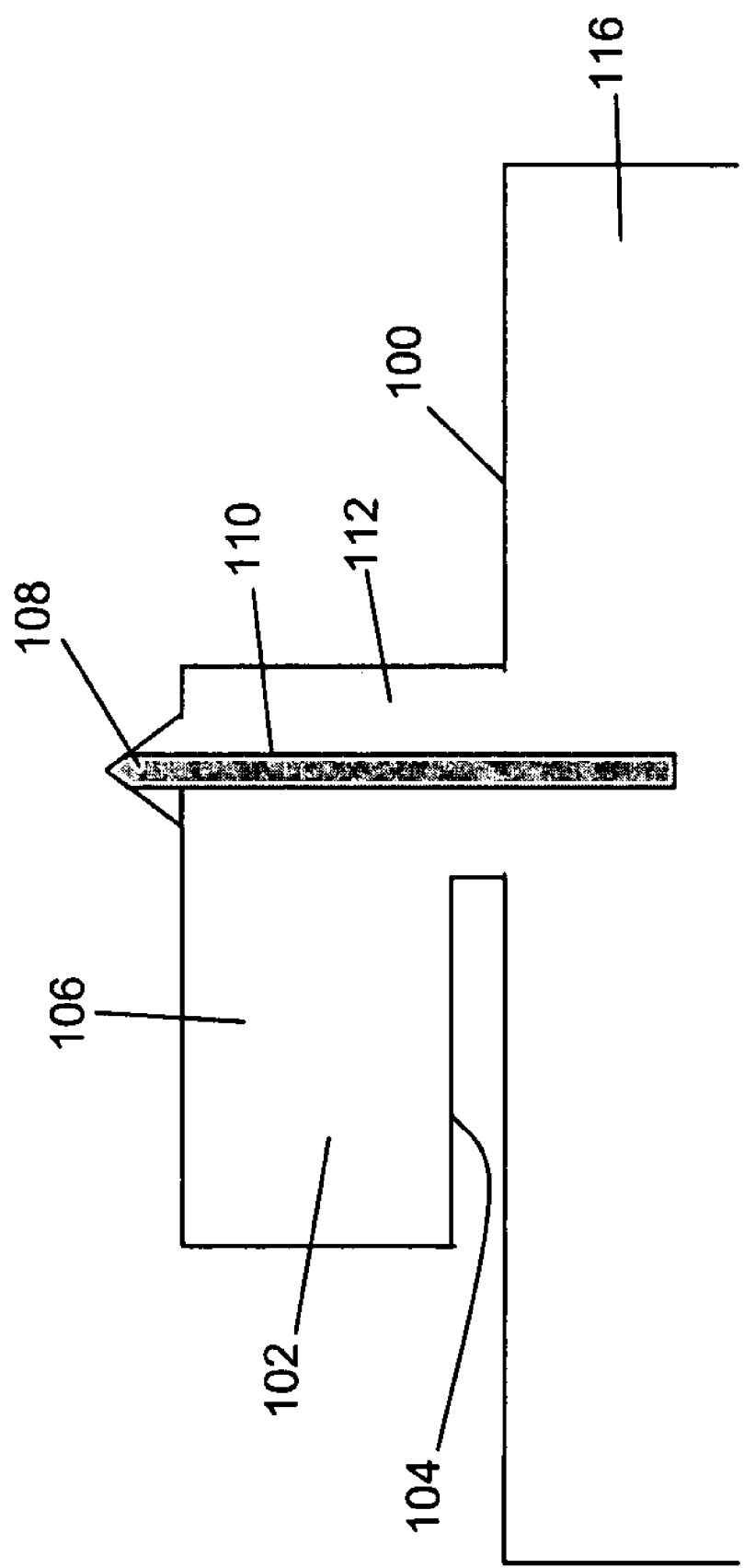
FIG. 1 is a schematic diagram of a pattern for a semiconductor bilayer that may be used to form a conducting tube having a conducting strip running along its inner surface.

The present invention provides microcoaxial probes that may be integrated as high-frequency tips in scanning probe microscopy systems. The microcoaxial probes are composed of conducting tubes, made from strained semiconductor bilayers. The microcoaxial probes include a conducting core channel and a conducting shield channel electrically insulated from the core channel.

The microcoaxial probes are capable of propagating electromagnetic signals and supplying such signals to a sample placed in close proximity to their probe tips. Thus, in one embodiment of the present invention, a microcoaxial probe may be coupled to a microwave frequency source such that a microwave field propagated by the probe may be applied to a sample of interest positioned close to the distal tip of the probe. The field transmitted by or reflected from the sample may be detected, for the purpose of carrying out microwave spectroscopy on the sample. Thus, the microcoaxial probes are well suited for use as scanning tips in microwave microscopy. However, the probes may also be adapted for use as tips in scanning tunneling microscopy and atomic force microscopy.

The conducting tubes are made from semiconductor heterostructures where tube formation is induced by the strain between the lattice mismatched semiconductor layers upon release of the bilayer from an underlying sacrificial layer. Examples of semiconductor bilayers that may be used to fabricate the conducting tubes in the microcoaxial probes include, but are not limited to, Si/SiGe bilayers and InGaAs/GaAs bilayers.

Methods of forming tubes from semiconductor bilayer heterostructures are described in Schmidt et al., Elsevier Materials Science and Engineering C 19, 393-396 (2002); Golod et al., Semicond. Sci. Technol. 16, 181-185 (2001); Prinz et al., Nanotechnology 12, 399-402 (2001); Prinz et al., Elsevier Science Physica E 6, 828-831 (2000); Schmidt et al., Appl. Phys. Lett., vol. 78 no. 21, 3310-3312 (21 May, 2001); and Schmidt et al., Elsevier Physica E 13, 969-973 (2002), the entire disclosures of which are incorporated herein by reference. Briefly, these methods involve the growth of a semiconductor bilayer on a sacrificial layer that initially holds the bilayer in place. Typically, the bilayer is grown on a semiconductor-on-insulator structure where a thin buried layer (e.g., a buried oxide) serves as the sacrificial layer. The growth of the bilayer may be carried out using standard deposition techniques, such as molecular beam epitaxy (MBE). The bilayer is then released from the sacrificial layer (e.g., by etching away the sacrificial layer). Upon release from the sacrificial layer, the bilayer curls towards the semiconductor layer with the smaller lattice constant, forming a coil which may be used as a conducting tube in a microscopy system. The wall thickness, conductance properties and diameter of the resulting tube will depend, at least in part, on the bilayer thickness, the degree of strain in the bilayer and the etching procedure. Therefore, by selecting appropriate semiconductor materials and processing conditions, tubes of various wall thicknesses and diameters may be fabricated. This is desirable because the modal spectrum of the electromagnetic waves that may be propagated in the conducting tube depends on the tube diameter. The present tubes may be fabricated with diameters of about 10 nm to about 300 microns and wall thicknesses of about 100 nm to about 5 microns. For example, some of the conducting tubes will have a diameter of no greater than about 5 microns. However, tubes with dimensions outside these ranges may be used, provided the wall thickness is small enough to allow for tube formation from the bilayer and the diameter is small enough to allow for the propagation of electromagnetic signals along the tube. The flexibility in the control of the tube diameter allows for the fabrication of coaxial probes capable of propagating electromagnetic waves with frequencies ranging from DC to THz.

The conducting channels in the microcoaxial probes may take various forms. In some embodiments, carrier confinement at the interface of two semiconducting layers in a semiconducting heterostructure (as in the case of a 2DEG) may provide a conductive channel. In some such embodiments, a 2DEG is formed between the two semiconductor layers of the strained bilayer. In some instances the conductive channels may have conductivities that are very close to the conductivities of metals. However, 2DEGs may also be provided between other layers of a multilayered heterostructure that includes the strained bilayer. In addition to, or as alternative to, conducting channels formed of low-dimensional electron gases, conducting channels may be provided by layers of highly doped semiconductors incorporated into a multilayered semiconductor structure. Alternatively, one or both conducting channels may be formed of layers of conductive material (e.g., metal films) that are deposited onto the inner and/or outer surfaces of the tubes. For example, a tube made from a strained bilayer may include a conducting strip, such as a thin metal strip, running along the length of its inner surface and terminating (preferably as an atomically sharp tip) at the distal end of the tube. The conducting strip may be patterned onto the surface of the "inner" layer of the bilayer, using standard deposition and patterning techniques, prior to coil formation.

Microcoaxial probes having atomically sharp probe tips are well-suited for use in STM and/or AFM in addition to (or as an alternative to) scanning microwave microscopy. The sharp point of the probe tip may be patterned into the semiconductor bilayer before coil formation, or it may be an artifact of the curling process that creates the coil.

FIG. 1 shows a schematic diagram of a pattern for a semiconductor bilayer that is suitable for use in fabricating a conducting tube with a conducting strip running along its inner surface. The strip may be evaporated onto the outer surface of the semiconductor bilayer prior to tube formation. For sufficiently thin metal layers (e.g., 10-100 nm) the presence of this thin film does not affect the curling process. As shown in this figure, a semiconductor heterostructure 100 supported on a sacrificial layer (not shown) is patterned (e.g., using conventional lithography) to define a tube section 102 having a proximal end 104 and a distal end 106. A point 108 is lithographically cut along the distal edge of the sheet and a strip of electrically conductive material 110 (e.g., gold) is deposited (e.g., evaporated) onto the inner surface 112 of the heterostructure 100, such that it extends to the point 108. Once the semiconductor bilayer of FIG. 1 has been fabricated, the tube section 102 of the bilayer may be released from the underlying sacrificial layer (e.g., by etching away the sacrificial layer). Once released, the tube section is allowed to curl into a conducting tube 114. The heterostructure pad 116, to which the conducting tube remains mechanically anchored, may be designed as a coplanar waveguide (not shown here) to transmit an electromagnetic signal, over a wide frequency band, to the inlet port 118 at the proximal end 104 of the conducting tube.

Figure 2:
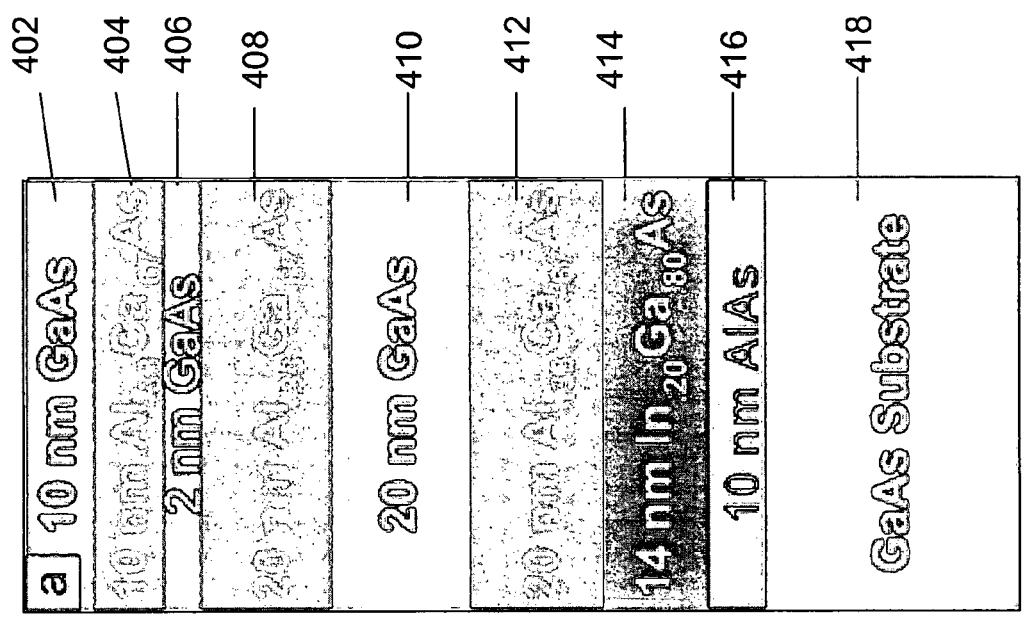
FIG. 2 is a schematic diagram of a cross-sectional view of a multilayered heterostructure that may be used to form a microcoaxial probe in accordance with the present invention.

To form a coaxial probe, the conducting tube of FIG. 2 may be coated with a thin layer of electrically conductive material that provides a grounded shield electrode 120. This coating is typically a thin layer of metal (e.g., gold) evaporated onto the outer surface of the conducting tube.

FIG. 2 shows a cross-sectional view of a multilayered semiconductor heterostructure that includes carrier confinement layers which may be used to form a microcoaxial probe in accordance with the present invention. The heterostructure includes a transport layer formed by a 10 nm GaAs cap layer 402 followed by a 10 nm $Al_{0.33}Ga_{0.67}As$ layer 404, a 2 nm GaAs (Si delta doped) layer 406, a 20 nm $Al_{0.33}Ga_{0.67}As$ layer 408, a 20 nm GaAs layer 410 over the strained bilayers of 20 nm $Al_{0.33}Ga_{0.67}As$ 412, 14 nm $In_{0.2}Ga_{0.8}As$ 414 and 10 nm AlAs (sacrificial layer) 416 over a GaAs substrate 418. When the sacrificial. AlAs layer is removed, the strained bilayer induces tube formation. In the tube, conducting channels are formed at the interface of the AlGaAs and InGaAs layers in the bilayer and between the 20 nm $Al_{0.33}Ga_{0.67}As$ and 20 nm GaAs layers.

The present microcoaxial probes may be used as scanning probes in microwave microscopy. In this application, the microcoaxial probes serve as a microwave resonator that is excited by a microwave signal propagating through the conducting tube. When the distal end of the probe is brought into close proximity to a surface, the resonant microwave signal may be altered by the presence of the surface. More specifically, the resonant frequency and the quality factor of the signal may be modified by the surface. By detecting the change in the microwave signal (i.e., either the change in resonant frequency, the change in the quality factor, or both) as the microcoaxial probe is scanned over the surface, information about the physical and chemical characteristics of the surface may be generated and converted into an image. The microcoaxial probes are capable of providing surface imaging with improved spatial and temporal resolution. For example, in some embodiments, the microcoaxial probes provide scanning microwave microscopy images having a spatial resolution of at least about 10 nm. This includes embodiments where the microcoaxial probes provide scanning microwave microscopy images with a spatial resolution of at least about 5 nm. The microcoaxial probes may be used with high-frequency signals, including signals with frequencies of 100 GHz, or greater.

The microcoaxial probes may be used as probes in a standard scanning probe microwave microscopy system, many of which are known and commercially available. Examples of scanning probe microscope systems may be found in U.S. Pat. No. 5,821,410; U.S. Patent Application Publication No. 2003/0034453; Tselev et al., Rev. Sci. Instr., 74, 3167-3170 (2003); and Park et al., Ultramicroscopy, 102, 101-106 (2005), the entire disclosures of which are incorporated herein by reference. A typical microwave microscopy system includes a microwave generator to feed a signal to the resonator, such as a voltage-controlled microwave oscillator, and a detector to probe the signal from the resonator (e.g., a diode detector or network analyzer), both of which are coupled to the microcoaxial probe resonator, e.g., via coupling antennae. A feedback circuit (e.g., a phase-locked loop circuit) may be used to keep the coaxial probe resonator locked onto the resonant frequency. A dc signal produced by the feedback circuit as it locks in the resonance frequency is proportional to the shift in resonance frequency caused by a surface at the distal end of the microcoaxial probe resonator and may be used to generate an image of the surface. At the same time, the quality factor of the microwave signal may be deduced from the power level measured by the detector. A sample having a surface of interest may be mounted below the coaxial probe, desirably on a scanning stage.

The microcoaxial probes may also be used as scanning tunneling microscope (STM) probes. The basic principle of an STM is based on the tunneling current between a conducting probe tip, which is sharpened to a single atom point, and a conducting material. A small bias voltage (e.g., mV to 3 V) is applied between an atomically sharp tip and the sample material. If the distance between the tip and the sample is large, no current flows. However, when the tip is brought very close ($\leqq 10$ Å) without physical contact, a current flows across the gap between the tip and the sample. This is the tunneling current which is the result of the overlapping wavefunctions between the tip atom and surface atom. Electrons can tunnel across the vacuum barrier separating the tip and sample in the presence of small bias voltage. The density of electronic states is the amount of electrons exiting at specific energy. Atomic information of the surface can be mapped out as a measure of the current with the tip moving across the surface.

The present microcoaxial probes may be used in an STM as follows: A microcoaxial probe having an inner conducting channel (e.g., a metal strip running along its inner surface) terminating in an atomically sharp tip (as shown, for example, in FIG. 2) is brought into close proximity to a surface of interest. A bias voltage is applied between the tip of the conducting channel at the distal end of the coaxial probe and the surface, inducing a tunneling current to flow between the conducting strip and the surface. By detecting the change in the tunneling current as the microcoaxial probe is scanned over the surface, the probe may generate information about the density of electronic states at the surface and convert that information into an image.

The microcoaxial probes may be used as probes in a standard scanning tunneling microscopy system, many of which are known and commercially available. A scanning tunneling microscope using a microcoaxial probe in accordance with the present invention may be described as follows: This system typically includes a current detector, such as a tunneling current amplifier, that detects the tunneling current, connected to a feedback circuit that keeps the tunneling current constant by manipulating a probe scanning stage (e.g., one or more piezoelectric actuators or a piezotube) which adjusts the distance between the surface and the end of the coaxial probe.

The microcoaxial probes may also be used as atomic force microscope (AFM) probes. The AFM works by scanning a fine tip over a surface. The tip is positioned at the end of a cantilever beam. As the tip is repelled by or attracted to the surface, the cantilever beam deflects. The magnitude of the deflection is captured by a laser that reflects at an oblique angle from the very end of the cantilever. A plot of the laser deflection versus tip position on the sample surface provides the resolution of the hills and valleys that constitute the topography of the surface. The AFM can work with the tip touching the sample (contact mode), or the tip can tap across the surface (tapping mode).

The present microcoaxial probes may be used in an AFM as follows: A microcoaxial probe having a conducting tube with a sharp point at its distal end is brought close to, or into contact with, a surface of interest. The microcoaxial probe is mounted to the end of a cantilever which deflects in response to the force between the point and the surface. By detecting the deflection of the microcoaxial probe as it is scanned over the surface, the probe may generate information about the topography of the surface and convert that information into an image.

The microcoaxial probes may be used as probes in a standard atomic force microscopy system, many of which are known and commercially available. An atomic force microscope using a microcoaxial probe in accordance with the present invention may be described as follows: This system typically includes the microcoaxial probe mounted to a cantilever. A sample having a surface of interest is mounted on a scanning stage, such as a piezotube, below the microcoaxial probe. A laser directs a beam of light onto the microcoaxial probe or cantilever. The reflected light is detected by a photodetector, such as a photodiode. The system may include a feedback circuit, coupled to the photodetector and the scanning stage, into which the signal from the photodetector is fed. The feedback circuit controls the scanning stage to keep the force between the point of the microcoaxial probe and the surface constant. The change in height of the scanning stage may then be used to generate an image of the surface. Alternatively, the deflection of the microcoaxial probe, as measured by the photodetector, may be used to generate an image of the surface, without feedback control.

Other components that may be included in the scanning microwave microscope, the scanning tunneling microscope, and the atomic force microscope include a computer which may be used to control the scanning stages, to save and process data, and to generate graphical images of the surfaces.

In some preferred embodiments, the microcoaxial probes of the present invention may be used in a microscopy system designed to carry out a combination of scanning microwave microscopy, scanning tunneling microscopy, and/or atomic force microscopy measurements on a surface. In these embodiments, the components of two or more such instruments could be combined into a single device, as needed.

EXAMPLES

The following examples describe methods for fabricating conducting tubes and microcoaxial probes from semiconductor bilayers. These examples are intended only to provide guidance for making and using this invention and are not intended to limit the scope of the invention.

Example 1

Fabrication of a Microtube from an Si/SiGe Semiconductor Heterostructure

A bilayer film was grown by deposition of Si onto an SiGe strained layer on insulator (SGOI) using solid-source molecular-beam epitaxy (MBE). The MBE SiGe film had a concentration of ~20% Ge. For the MBE film, the thickness of Si layer was controlled by rotating a shutter in the MBE chamber. The growth rate was 0.55 Å s$^{-1}$ at a substrate temperature of 585° C., measured by an optical pyrometer. The MBE growth of the Si layer was monitored by reflection high-energy electron diffraction during the entire growth process.

The SGOI substrate was obtained from SOITEC (France). The thickness and composition of SGOI were about 44 nm Si with 20% Ge on 190 nm SiO$_2$. The sample was cleaned with 10% hydrofluoric acid to remove the native oxide grown in air on the original SGOI surface, followed by 10 min of cleaning with piranha (H$_2$SO$_4$/H$_2$O$_2$), and a few seconds 10% HF etching to remove the oxide layer produced during the piranha treatment.

Photolithography and electron-beam lithography were performed to pattern the thin films into cantilevers. An array of cantilevers with different dimensions and orientations was created on each side of a 50 μm×50 μm square. The common width of the (100) cantilever was 3 μm and the lengths varied from the longest to the shortest as 20, 15, 10, 6, and 3 μm. The spacing in between was 5 μm. The width of the (110) cantilever was 6 μm and the length varied as 36, 26, 16, 6, and 4 μm. The spacing in between was 2 μm.

After lithography, the desired patterns were transferred onto the Si/Si$_{0.8}$Ge$_{0.2}$ bilayer film by using O$_2$ and SF$_6$ reactive-ion etching. The underlying sacrificial oxide layer was selectively etched off by the vapor of HF acid to release the cantilever, which bended upward and folded into microtubes. The HF vapor-releasing process was carried out at a temperature of 40° C. with a time duration of 30-60 min. In some instances the microtubes formed cylinders and in others the microtubes formed coils, depending upon the direction in which the crystals were patterned with respect to the underlying crystal symmetry. Both geometries are suitable for the production of microcoaxial probes. (For the purposes of this disclosure, curled tubes that form cylinders, coils, or other rolled geometries are all referred to as "coiled semiconductor bilayers.") The microtubes support circularly polarized electromagnetic signals. One important advantage of this technique is that it is a single process without subsequent rinsing steps, thus preventing the released structures from sticking onto the substrate. Also, for this purpose, it was desirable to create a strain configuration, with an Si film grown on top of SiGe by using the unique SGOI wafer.

Example 2

Fabrication of a Microtube from an Si/SiGe Semiconductor Heterostructure

Figure 4:
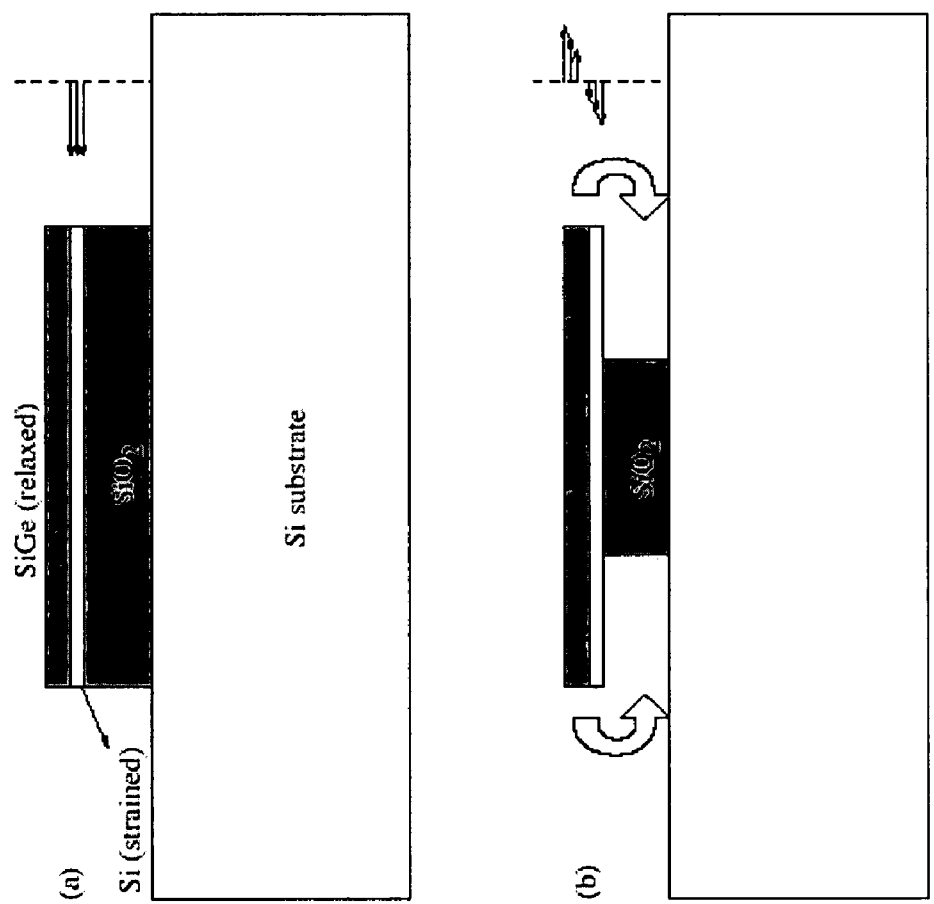
FIGS. 4(a) and (b) schematically illustrate the release of a Si/SiGe bilayer from a substrate.

Arrays of squares were patterned on SiGe/Si bilayer material (obtained from SOITEC (France)) using electron-beam lithography, aluminium deposition, and lift-off. Reactive-ion etching was used to isolate the bilayer squares from each other. Each array contained 400 squares with identical dimensions. As schematically shown in FIG. 4(a), the bilayer includes a 50-nm-thick layer of relaxed Si$_{0.8}$Ge$_{0.2}$ over a 20-nm-thick layer of strained silicon. The 184-nm-thick SiO$_2$ layer served as a sacrificial layer. This heterostructure was realized using the Smart Cut technology, in which the strained silicon layer was initially grown on relaxed Si$_{0.8}$Ge$_{0.2}$ and then both layers were transferred to a SiO$_2$ sacrificial layer on the Si substrate. Both planes of the bilayer and substrate were oriented along crystalline direction (001). Squares were patterned so that the edges were parallel to the (110) (±5°) direction and the diagonals lied along the (010) (±5°) direction. The induced strain from the lattice mismatch between the Si$_{0.8}$Ge$_{0.2}$ and Si layer was found to be $\epsilon \approx 4.2\% \times x = 8.4 \times 10^{-3}$, where x=0.2 is the Ge fraction in the Si$_{0.8}$Ge$_{0.2}$ layer and 4.2% is the lattice mismatch between silicon and germanium. To remove the SiO$_2$ sacrificial layer, hydrofluoric acid buffered by ammonia fluoride (NH$_4$F:HF=6:1) was used at room temperature. As illustrated in FIG. 4(b), once released from the substrate, the bilayer curved downward and some of the strain was transferred to the SiGe layer due to the initial compressive strain in the silicon layer. After etching, the samples were transferred into deionized water to remove the etchant. Before the samples were dried in air, acetone and isopropanol rinsing steps were applied.

Figure 3:
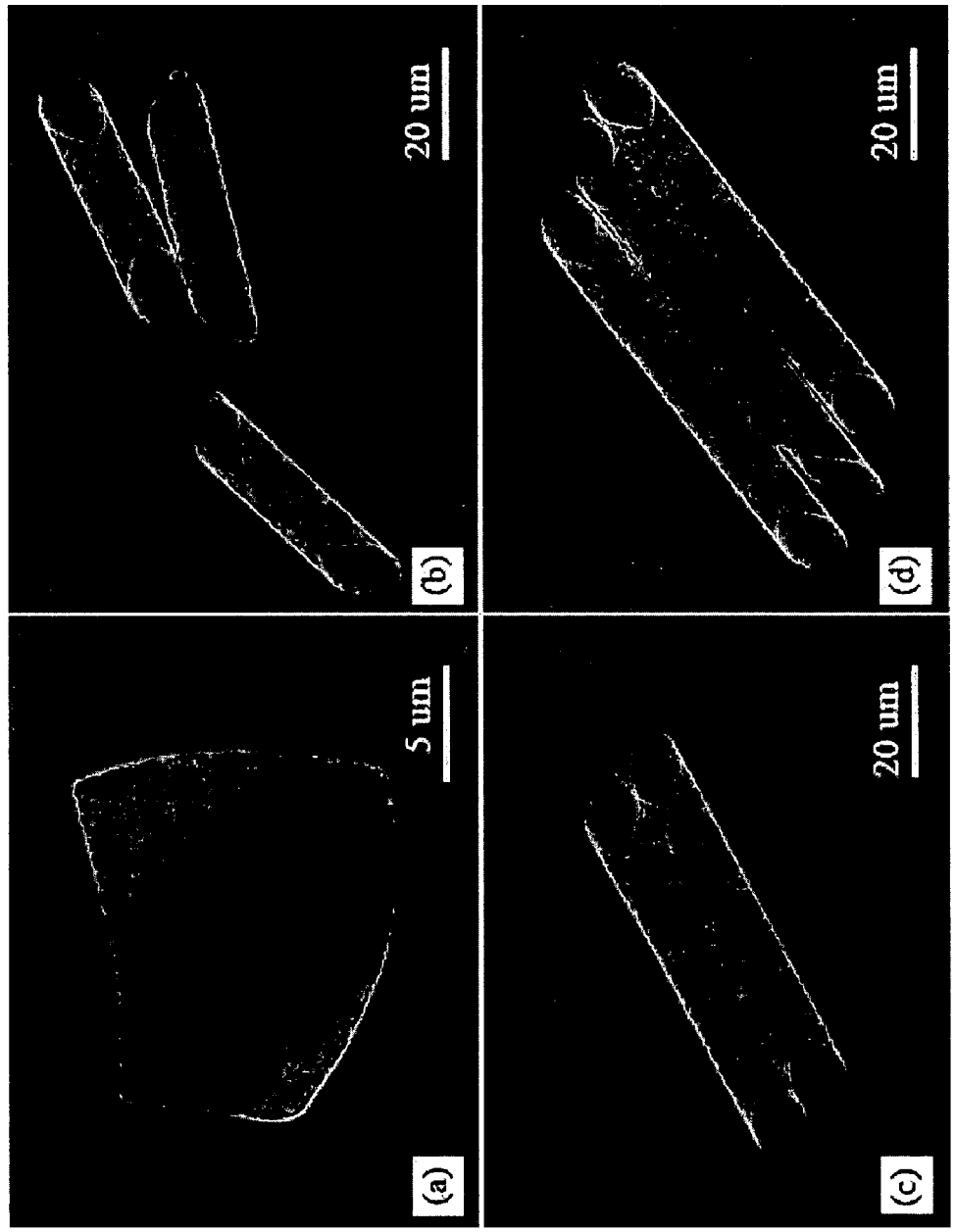
FIGS. 3(a)-(d) show scanning-electron micrographs of Si/SiGe bilayers.

FIGS. 3(a)-(d) show scanning-electron micrographs of Si/SiGe bilayers. FIGS. 3(b)-(d) show microtubes formed from the Si/SiGe bilayers.

Example 3

Fabrication of a Microtube from an InGaAs/GaAs Semiconductor Heterostructure A heterostructure comprising a transport layer formed by 10 nm GaAs cap layer, followed by 10 nm Al$_{0.33}$Ga$_{0.67}$As layer, 2 nm GaAs (Si delta doped) layer, 20 nm Al$_{0.33}$Ga$_{0.67}$As layer, 20 nm GaAs layer over the strained bilayers of 20 nm Al$_{0.33}$Ga$_{0.67}$As, 14 nm In$_{0.2}$Ga$_{0.8}$As and 10 nm AlAs (sacrificial layer) over a GaAs substrate was used to make a microcoaxial probe. The heterostructure is shown schematically in FIG. 2. The sacrificial AlAs layer was removed by immersing the heterostructure in a 1% HF solution. Upon release of the heterostructure from the sacrificial layer, the built-in strain in the bilayer caused the heterostructure to form a microtube. Carrier confinement channels at the interface of the AlGaAs and InGaAs layers in the bilayer and between the 20 nm Al$_{0.33}$Ga$_{0.67}$As and 20 nm GaAs layers provided the conducting core and shield layers in the microcoaxial probes.

For the purposes of this disclosure and unless otherwise specified, "a" or "an" means "one or more." All patents, applications, references, and publications cited herein are incorporated by reference in their entirety to the same extent as if they were individually incorporated by reference.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like includes the number recited and refers to ranges which can be subsequently broken down into subranges as discussed above. Finally, as will be understood by one skilled in the art, a range includes each individual member.

It is understood that the invention is not confined to the particular embodiments set forth herein as illustrative, but embraces all such modified forms thereof as come within the scope of the following claims.

What is claimed is:

1. A microcoaxial probe for a scanning microwave microscope comprising:
   (a) a conducting tube comprising a coiled semiconductor bilayer comprising two conducting channels, the tube having a proximal end and a distal end;
   (b) a microwave generator coupled to the conducting tube and adapted to feed a microwave signal to the proximal end of the tube; and
   (c) a detector coupled to the conducting tube and adapted to probe a microwave signal reflected from a surface.

2. The probe of claim 1, wherein the distal end of the conducting tube comprises an atomically sharp tip.

3. The probe of claim 1, wherein at least one of the conducting channels comprises a metal film deposited on an inner or outer surface of the conducting tube.

4. The probe of claim 3, wherein the bilayer comprises an Si/SiGe bilayer.

5. The probe of claim 1, wherein the semiconductor bilayer comprises an AlGaAs/InGaAs bilayer.

6. The probe of claim 1, wherein at least one of the conducting channels comprises a two-dimensional electron gas.

7. The probe of claim 1, wherein both of the conducting channels comprise a two-dimensional electron gas.

8. The probe of claim 1, wherein at least one of the conducting channels comprises a doped semiconductor.

9. The probe of claim 1, wherein both of the conducting channels comprise a doped semiconductor.

10. The probe of claim 1, wherein the conducting tube has an inner diameter of no more than 5 microns.

11. A scanning microwave microscope comprising the probe of claim 1, wherein the conducting tube is coupled to a detector adapted to detect an alteration in the microwave signal.

12. The scanning microwave microscope of claim 11, further comprising a surface mount disposed below the conducting tube and an xy-scanning control connected to the surface mount.

13. The scanning microwave microscope of claim 11, further comprising a computer for converting the output of the detector into an image of the surface and a graphical display for displaying the image.

14. A method of imaging a surface using microwave microscopy, the method comprising:
   (a) bringing the distal end of the conducting tube of the microcoaxial probe of claim 1 into close proximity to the surface;
   (b) providing a microwave signal to the conducting tube, thereby creating a microwave resonator wherein the surface is sufficiently close to the distal end of the conducting tube to alter the microwave signal; and
   (c) measuring the alternation in the microwave signal as the microcoaxial probe scans the surface.

15. A scanning tunneling microscope comprising:
   (a) a conducting tube comprising a coiled semiconductor bilayer comprising two conducting channels, the tube having a proximal end and a distal end; and
   (b) a voltage source coupled to the conducting tube for applying a bias voltage to the conducting tube; and
   (c) a current detector coupled to the conducting tube for measuring a tunneling current from the conducting tube to the surface.

16. A method of imaging a surface using scanning tunneling microscopy, the method comprising:
   (a) bringing the distal of the conducting tube of the microscope of claim 15 into close proximity to the surface;
   (b) applying a bias voltage between the distal end of the conducting tube and the surface, wherein the surface is sufficiently close to the distal of the conducting tube for a tunneling current to flow between the conducting tube and the surface; and
   (c) measuring the tunneling current as the conducting tube scans the surface.

17. An atomic force microscope comprising:
   (a) a conducting tube comprising a coiled semiconductor bilayer comprising two conducting channels, the tube having a proximal end and a distal end, the conducting tube mounted on a cantilever;
   (b) a laser positioned to direct a beam of light onto the cantilever; and
   (c) a photodetecter positioned to detect reflected light from the cantilever.

18. A method of imaging a surface using atomic force microscopy, the method comprising:
   (a) bringing the distal end of the conducting tube of the microscope of claim 17 into close proximity to, or into contact with, the surface;
   (b) scanning the distal end of the conducting tube over the surface, wherein the surface is sufficiently close to the distal end of the conducting tube to deflect the conducting tube as the point is repelled by or attracted to the surface; and
   (c) measuring the deflection of the conducting tube as it scans the surface.

19. A microcoaxial probe comprising:
   (a) a conducting tube comprising a coiled semiconductor bilayer comprising two conducting channels, the conducting tube having a proximal end, a distal end, an inner surface, and an outer surface; and
   (b) a metal film disposed on at least one of the inner and the outer surfaces of the conducting tube.

20. The microcoaxial probe of claim 19, wherein one of the conducting channels comprises a two-dimensional electron gas.

21. The microcoaxial probe of claim 19, wherein one of the conducting channels comprises a doped semiconductor.

22. The microcoaxial probe of claim 19, wherein the semiconductor bilayer comprises an Si/SiGe bilayer.

23. The microcoaxial probe of claim 19, wherein the conducting tube has an inner diameter of no more than about 5 microns and the combined thickness of the conducting tube and the metal film is no greater than 200 nm.

* * * * *